(12) United States Patent
Ngo et al.

(10) Patent No.: US 10,434,208 B1
(45) Date of Patent: Oct. 8, 2019

(54) INTEGRATED DISINFECTION SYSTEM

(71) Applicants: Phuc Ngo, San Jose, CA (US); Kris Le, San Jose, CA (US); Vidyadhar Handragal, San Jose, CA (US)

(72) Inventors: Phuc Ngo, San Jose, CA (US); Kris Le, San Jose, CA (US); Vidyadhar Handragal, San Jose, CA (US)

(73) Assignee: Zuna Inc., San Jose, CA (US)

( * ) Notice: Subject to any disclaimer, the term of this patent is extended or adjusted under 35 U.S.C. 154(b) by 0 days.

(21) Appl. No.: 15/975,698

(22) Filed: May 9, 2018

(51) Int. Cl.
| | |
|---|---|
| *A61L 9/20* | (2006.01) |
| *A01G 9/26* | (2006.01) |
| *H05B 37/00* | (2006.01) |
| *A01G 9/24* | (2006.01) |
| *H05B 37/02* | (2006.01) |

(52) U.S. Cl.
CPC ............... *A61L 9/20* (2013.01); *A01G 9/246* (2013.01); *H05B 37/0272* (2013.01); *H05B 37/0281* (2013.01); *A01G 9/26* (2013.01); *A61L 2209/12* (2013.01)

(58) Field of Classification Search
CPC ... A61L 19/20; A61L 19/246; H05B 37/0272; H05B 37/0281; A01G 9/26; A01L 2209/12
USPC ............... 250/453.11, 454.11, 455.11, 504 R
See application file for complete search history.

(56) References Cited

U.S. PATENT DOCUMENTS

| | | | |
|---|---|---|---|
| 7,807,101 B2 | 10/2010 | Mason | |
| 2003/0170152 A1* | 9/2003 | Kobayashi | ............... A61L 2/10 422/186.3 |
| 2005/0079123 A1 | 4/2005 | Shuler | |
| 2009/0272029 A1 | 11/2009 | Aiking | |
| 2017/0049915 A1* | 2/2017 | Brais | .................. H05B 37/0227 |

\* cited by examiner

*Primary Examiner* — Nicole M Ippolito

(57) ABSTRACT

A mold disinfection system includes: a first compartment with an air inlet, an air pump to circulate air, a UVC lamp to disinfect mold in the circulated air, and an air outlet; a second compartment with one or more doors and a mirror on each door to reflect UVC radiation; a third compartment with a door and a mirror on the back of the door to reflect UVC radiation; wheels extending from one of the compartments to move the system; and electronics controlling the UVC lamps and the air pump and communicating with a mobile device to receive operating instructions therefrom.

19 Claims, 5 Drawing Sheets

INTEGRATED DISINFECTION SYSTEM

BACKGROUND

The invention pertains to disinfection of the mold spores in a grow facility.

Mold can be found everywhere. They can grow on almost any surface where moisture is present. Molds reproduce by spores, which are carried by air currents. When spores land on a moist surface, that is suitable to sustain life, mold begins to grow. Indoor and outdoor gardens or grow spaces are normally prone to be affected by both mold and mildew. They are probably more pronounced in indoor grow spaces.

Mold is a strong threat to *cannabis*, and an outbreak can be detrimental to an entire crop. Mold can have an adverse impact on the growing plants, if not controlled. The mold spores can accumulate on floors, spread via air currents, brought indoors via clothes and shoes. Additionally, mold can develop on marijuana plants, buds or seeds due to moisture and humidity. This can be because of poor ventilation in a closed in facility, or if the pot is packaged in air-tight containers with significant moisture in the buds. Since commercial grow houses tend to be large operations, the presence of more plants allows more chance of mold growing and spreading. The same ingredients which help with high yields also help create a perfect environment for the mold spores to thrive on. Molds can form at all stages of the plant growth and harvest cycle:

Growth Stage: A common location for mold to occur is within the grow room. If mold begins to spread from plant to plant, many, if not the entire crop, can be destroyed. A complete kill of microbial contaminants is necessary to prevent mold occurrence and must be achieved prior to any plants entering the space. A complete sanitization will ensure there are no lingering spores in the environment that could spread and wreak havoc once growing begins. Traditional methods of cleaning may not account for airborne mold spores, spores hidden in cracks or tight spaces, and human limitations.

Drying Stage: A large percentage of mold begins after harvest. During the drying process, mold will form if the moisture level is too high. If air quality is left unmonitored, mold spores will grow. As long as buds have at some water or moisture content, it risks the development of mold. Buds can develop pockets of humid air, which are strong risk sites. If buds are too dry, growers sometimes place fruit peels amongst them to add moisture and flavor. However, this can introduce mold into the environment if the fruit is contaminated and spread spores to the *cannabis* buds.

Curing Stage: Once *cannabis* is at the correct state, the plant can be put into jars or airtight totes to begin the curing phase. Moisture from the stems and buds will seep into the air within the enclosed space and be exposed to the rest of the buds. This moisture removes impurities from the buds. This moisture also places buds at risk for mold growth. A grassy smell may indicate it has not been cured long enough and residual moisture may lead to mold.

The design of indoor grow rooms for medical marijuana can be critical to the control of airborne fungal spores and the microbes residing on various surfaces. It is common knowledge that most existing grow houses are poorly suited to prevent the ingress of fungal spores. The prevailing solutions include either a new design or retrofitting a series of air filters, fans, and UV systems to render the grow spaces relatively free of spores and other microbial contaminants.

Normal disinfection or decontamination procedures such as the ones used in hospital environments or cleanrooms are currently adapted for plant grow rooms. Some of the known practices are listed below:

a. Traditional fungicides that may leave hazardous residues.

b. Air particulate filtration systems that maintains the indoor growing area free of airborne fungal spores c. Chlorine dioxide gas decontamination d. Manual Spray, Wipe and Soaking with liquid disinfection solutions.

e. Use of UV-C disinfection lamps

Each of the above methods has its own significant limitation, particularly with regards to the microbial "kill" effectiveness.

Privatized and legally commercial medical marijuana grow operations are relatively safer since these facilities are subjected to annual inspections and reviews. Nonetheless, any mold growth could still present a health hazard. Although, State licensing standards require marijuana growers and the manufacturers of marijuana infused product to "take reasonable measures and precautions" to store the drug in a way that prevents the rapid growth of microorganisms, but this is very subjective. The State laws are still trying to catch up with the growth of operations in general. Most, if not all the universal building code manuals make no mention of indoor marijuana grow operations at this stage.

SUMMARY

In one aspect, a mold disinfection system includes: a first compartment with an air inlet, an air pump to circulate air, a UVC lamp to disinfect mold in the circulated air, and an air outlet; a second compartment with one or more doors and a mirror on each door to reflect UVC radiation; a third compartment with a door and a mirror on the back of the door to reflect UVC radiation; wheels extending from one of the compartments to move the system; and electronics controlling the UVC lamps and the air pump and communicating with a mobile device to receive operating instructions therefrom. The mirrors can be metallic reflectors with special coatings that offer very high transmittivity for UV light.

In another aspect, a mold disinfection system includes: a first compartment with an air inlet, an air pump to circulate air, a UVC lamp to disinfect mold in the circulated air, and an air outlet; a second compartment with one or more doors that allow passage of UVC radiation; a third compartment with a door that passes UVC radiation; wheels extending from one of the compartments to move the system; and electronics controlling the UVC lamps and the air pump and communicating with a mobile device to receive operating instructions therefrom.

In third aspect, a mold disinfection system includes: a first compartment with an air inlet, an air pump to circulate air, a UVC lamp to disinfect mold in the circulated air, and an air outlet; a second compartment with mirrors to reflect UVC radiation; a third compartment with a door that passes UVC radiation therethrough; wheels extending from one of the compartments to move the system; and electronics controlling the UVC lamps and the air pump and communicating with a mobile device to receive operating instructions therefrom.

Advantages of the system may include one or more of the following. The system is multifunctional, portable, movable and remotely operable, so various spaces within the facility and at various grow stages of the plants, can be disinfected. The system provides a remote disinfection system using UVC light source that can be remotely controlled and operated. The system efficiently disinfects airborne and surface micro-organisms. The system provides a cost effective, highly repeatable and easy to use system that is portable and movable, so various spaces can be disinfected within the grow facility. The system provides seamless integration with existing (e.g. air purification systems, etc.) control procedures in place. As marijuana becomes a more accepted form of medicine for seriously ill patients, the system helps growers by ensuring that plants and people are protected from the effects the mold or microbial contaminants might have on them.

BRIEF DESCRIPTION OF THE DRAWINGS

The present invention will be discussed in more detail below, using a number of exemplary embodiments, with reference to the attached drawings, in which:

FIG. 5 shows the system of FIG. 1 in an open condition, while

DETAILED DESCRIPTION

Figure 1:
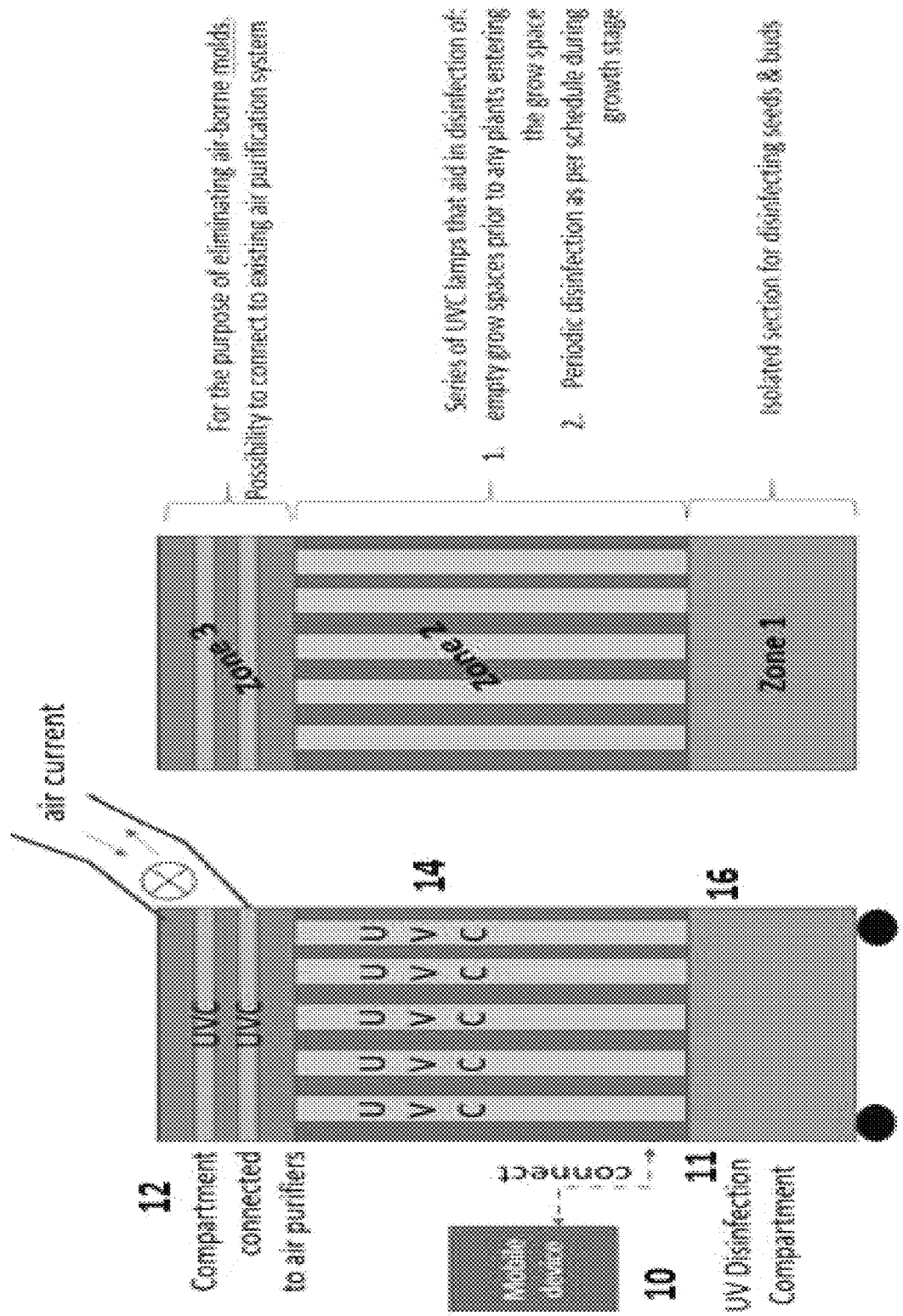
FIG. 1 shows an exemplary mold disinfection system.

FIG. 1 shows an exemplary mold disinfection system 11 controlled by a mobile device 10. The device 10 wirelessly communicates with controllers in the system 11. System 11 has a plurality of compartments 12-16 defining various zones. The system 11 uses a quick, chemical-free, highly effective method of disinfection through ultraviolet light (UVC or UV-C). UV-C is the spectrum of light that will kill harmful organisms and spores within minutes. Unlike a gas that can result in complete distribution of the decontaminating agent, UV-C will only kill the microbes on surfaces where light is emitted onto or targeted.

"UV-C light" or "UV-C radiation" refers to ultraviolet light (or radiation) having a wavelength of between 240 and 260 nm. UV-C light, having a wavelength of between 243 and 255 nm is preferred; in some embodiments, a wavelength of between about 245 and 247 nm is particularly preferred, as it has been observed that the anti-pathogenic effect of UV-C light tends to peak at this wavelength range. This definition encompasses wavelengths of 240-260 nm, as well as the end-point values as such or values or ranges in between the end-points, such as about 254 nm or about 260, 261, 262, 263, 264 or 265 nm. UV light can be divided into different classes based on wavelength, including ultraviolet A (UV-A) at about 350 nm, ultraviolet B (UV-B) at about 300 nm and ultraviolet C (UV-C) at about 250 nm. Not unexpectedly, the effectiveness of UV light in producing biological changes can differ at different wavelengths. For fungal treatment, the use of UV light is attractive in that it is a non-chemical treatment that leaves no toxic residue on the crop or in the environment. It has been demonstrated that UV light can inactivate fungal growth. However, UV-A and UV-B have been shown to cause damage to human skin end human eyes. Furthermore, UV-A and UV-B have been demonstrated to be carcinogenic, whereas UV-C is reportedly not carcinogenic.

Ultraviolet light is a specific part of the electromagnetic spectrum of light that offers bactericidal effects. Ultraviolet light is divided into UV-A, UV-B, and UV-C rays. It is the wavelengths in the UV-C spectrum which offer great germicidal potential. When a microorganism is exposed to UV-C, the nuclei of the cells are altered due to photolytic processes. This process prevents further replication and causes cell death. Therefore, UV-C can provide high level disinfection of many viruses, bacteria, fungi, and spores.

In the embodiment of FIG. 1, the Integrated system consists of three different compartments performing three different functions as follows:

Zone 1 (Enclosed Sanitization): The seeds can be placed inside this compartment that consists of a series of UVC lamps that are placed radially, or other desired configuration, thereby enabling the seeds and buds (during curing) to experience 360 degrees of direct UVC coverage. This results in a significant kill of any surface mold without harming the seed.

Zone 2 (Open Space Sanitization): This is essentially a compartment that has a series of high powered UVC lamps that are positioned towards the outer wall of the system. The UVC lamps are covered by another layer of plastic or sheet metal enclosure to prevent accidental damage and unwanted UVC exposure to humans. The enclosure panels open only during operation.

Zone 3 (In-duct Sanitization): A compartment that has a series of UVC lamps built inside. This compartment can be connected via a duct to the existing air purifiers wherein the air-borne mold can be directed thru a forced air current (achieved by creating turbulence via axial fans) and passing the air through the UVC lamps and further redirecting the air back to the air purification system. This is very efficient in killing the powdery mildew and other mold types that can recirculate through the ventilation systems.

A duct can be connected to supply or return ducts of the existing air purifiers. The long air flow paths will ensure substantial contact time with the air stream with the UVC lamps. The duct design can include various disinfection sizing calculations such as air speed, dimensions of the ducts and the UVC intended dosage. One embodiment installs a variable speed axial motor that can create air turbulence to ensure effective recirculation of the air stream to maximize the "killing" of mold spores in the available air stream.

The Remote hand-held App and Mobility is detailed next. The entire system can be controlled remotely through an application on a hand-held device such as a tablet or mobile device 10. The remote control will ensure that humans are not impacted due to potential harmful effects of the UVC radiation. Additionally, the App on the mobile device can include reception of various data such as UV Dosage, Operator Name, Room Number, and Time/Date. The application can be further synced with an existing schedule or to create a new schedule towards any Contamination Control Program as devised by the Grow Facility or defined by State Regulators.

A transfer function or an algorithm is inbuilt that manages/controls the UVC disinfection by a variable switch that controls the two factors for disinfection depending on the mold spore or microbial contaminant in question. The selection of the UVC lamps can be adaptable or engineered considering that sufficient intensity is required to deliver the sterilization dosage within a reasonably short amount of time, typically less than a minute exposure.

1. Contact time (exposure of UVC light with the contaminant)
2. UVC output and intensity All systems can be operated remotely with tablets or mobile devices. The embodiment of FIG. 1 has wheels on the bottom to move the disinfection system into the room for operation. Additionally, the system has a software that allows them to capture utilization data, including treatment time, location usage, and operator statistics. In context with the remote wireless UV-C measurement sensors, the software also tracks delivered dose and utilization data in real time. The system calculates the dose to be delivered (dose=UV-C intensity×time of exposure to the UVC) based on the dimensions of the room and can be set on a timed interval. The system can also have sensors on the emitter that measure the light reflected back to the device from surfaces within the room. It can use remote wireless sensors placed in different targeted areas of the room to measure incident light (both reflective and direct) and therefore actual dose delivered.

The system's software has a feature for metrics-driven tracking system. The operator enters the room data and later key pieces of data can be correlated, such as actual dose delivered to individual rooms/section, average room treatment times, operator variability regarding room turnaround time, and device utilization over time. Due to the ability for data capturing and tracking capability of the system, a schedule for regular software reporting reviews can be done that will further aid to affect a quality control schedule, manage compliance issues, assess utilization patterns and analyze the need for operator training or retraining.

The system also tries to address various operational and usability factors such as the need for rapid room turnover (faster use times lead to more rapid room turnover, the opportunity to treat more rooms in a shorter period. Additionally, the system has intelligence with a "pause and reposition" capability that allows the operator to pause the system say after 2 remote sensors have reached their predetermined dose and reposition the device to trigger other target area disinfection. This will enable optimum utilization of the system.

The system is built to be powered by rechargeable batteries with a provision for powering through a wall outlet. The castor wheels enable desired movement for placing the system in the grow space to commence disinfection. The additional set of wheels provided ensure remote mobility through the application that can follow the defined or predefined route in the grow premises.

Figure 2:
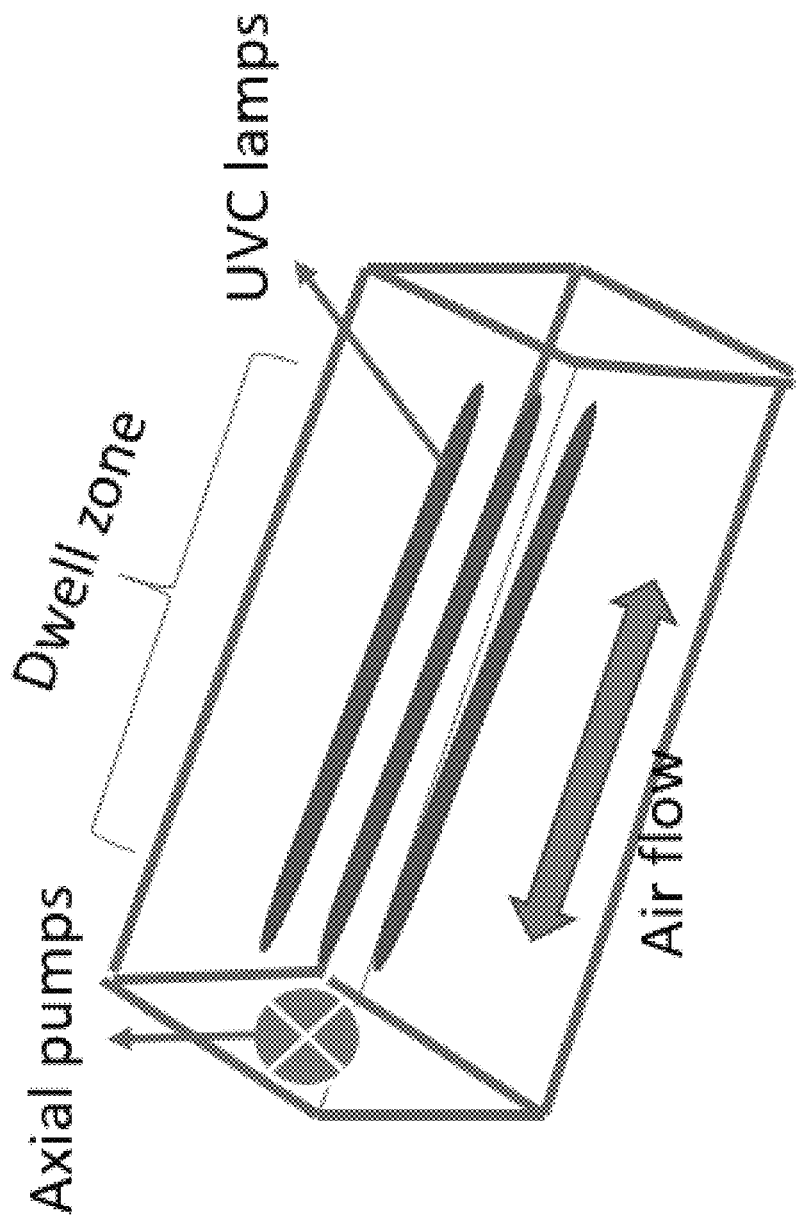
FIG. 2 shows in more details an exemplary layout of a compartment in the system of FIG. 1.

FIG. 2 shows in more details an exemplary layout of Zone 3 Compartment 12. The compartment 12 has axial air pumps that move air flow within a dwell zone. In one embodiment, Zone 3 is specifically designed to control the "powdery mildew" by connecting to existing filtration and the air stream sterilized by delivering a sufficiently high germicidal UVC dose from UVC lamps. One embodiment provides a compartment effective at controlling mold such as "*Botrytis*" and other fungal contaminants. The lamp provides a light source of UV-C light; wherein the light source emits essentially no UV-A and UV-B light; but at least 90%, 95%, 98%, 99% or more of only UV-C light. Optionally the light source further comprises a quartz tube or casing around it, so that UV-C emission is not reduced and dust and dirt does not collect on the light source itself but on the quartz tube; the dust and dirt can be easily removed by e.g. using high pressure sprayers (spraying e.g. water). Optionally the quartz tube may further comprise a Teflon layer on the inside and/or outside, so that breakage or damage of the quartz tube does not result in particles scattering; essentially all broken particles remain attached to one another by the Teflon layer and the light source can be replaced easily. A transportation module is provided for passing the light source by the plant (or at least a plant part), wherein during one pass of the plant by the light source the plant (or plant part) is treated with an amount of UV-C light which is high enough to reduce (or prevent) plant tissue damage caused by said pathogens but which is low enough not to damage permanently said plant. In one embodiment, the UV-C light is high enough to control (especially reduce) the pathogen growth, while at the same time it does not have a negative effect on the growth, development and/or yield of the plant.

By passing the light source by a plant or the plant by a light source the plant (or plant part) will be exposed for a predetermined limited time. In this limited time the pathogen growth will be controlled, especially reduced. Consequently, the overall amount of pathogen biomass and infection by pathogens is decreased, giving the plant time to recover from the infection. This recovery enables the plant to grow healthier, resulting in superior crop yield.

In a further embodiment, the amount of UV-C light is between 0.002 (or 0.0025) and 0.16 J/cm2 during a period of 24 hours, more preferably between 0.002 (or 0.0025) and 0.15 J/cm2, especially equal to or below 0.16 or 0.15 J/cm2. A fluence in this range in a tissue of a plant is suitable to control the pathogens and that surprisingly only very low UV-C dosages are required to achieve and effective control. The optimal value of fluence depends on the plant species, the growth stage, type of pathogen and growth stage of the pathogen.

Figure 3A:
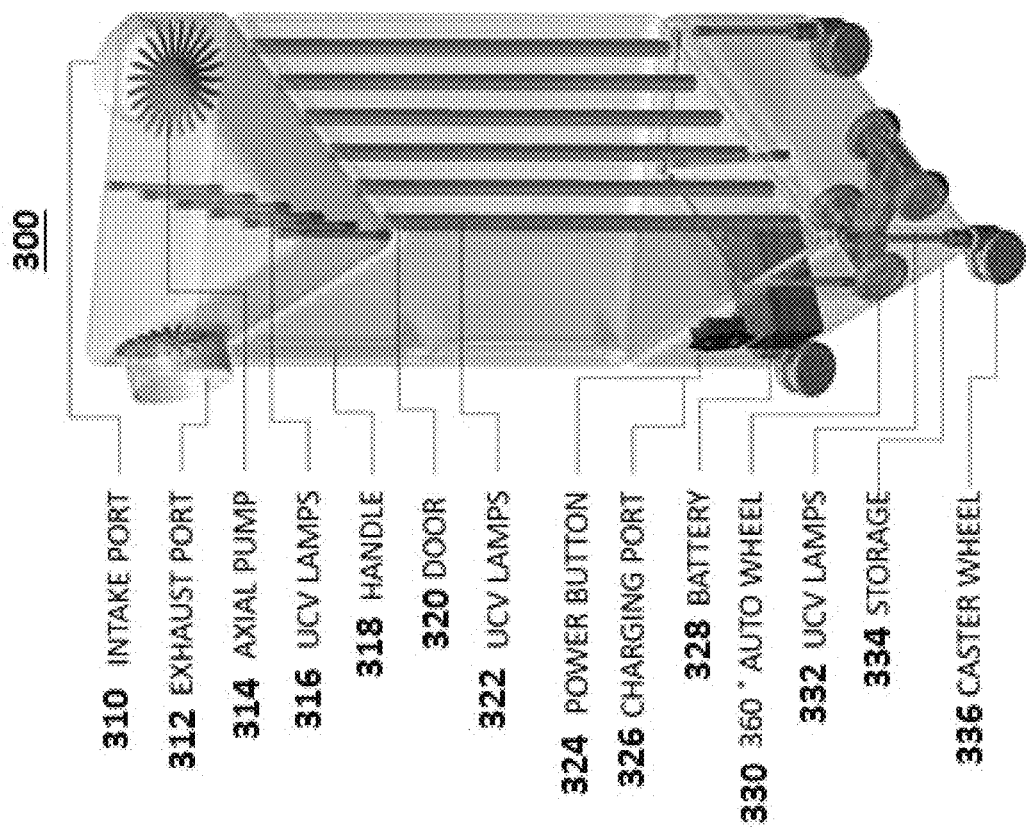
FIGS. 3A-3B show a cut-away view and a perspective view of the integrated mold disinfection system or unit.
Figure 3B:
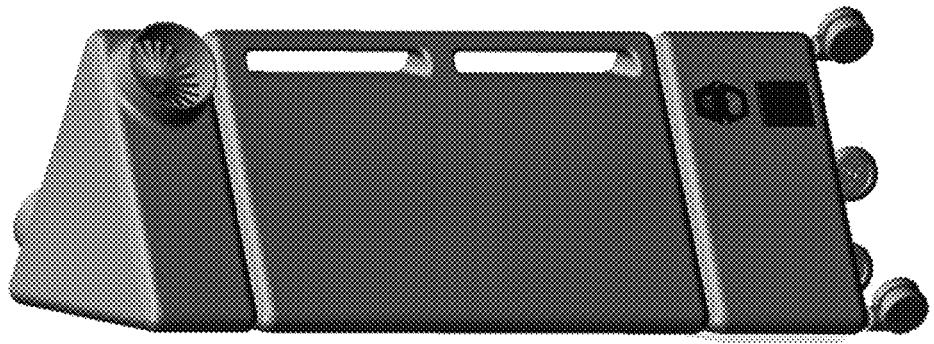

FIGS. 3A-3B show a cut-away view and a perspective view of the integrated unit 300. In FIG. 3A, the unit 300 has an air intake port 310 that receives air and exposes the circulating air to UCV lamps 316 to disinfect the air of the mold. The intake port 310 is powered by an axial pump 314 and air is then vented out an exhaust port 312.

Figure 5:
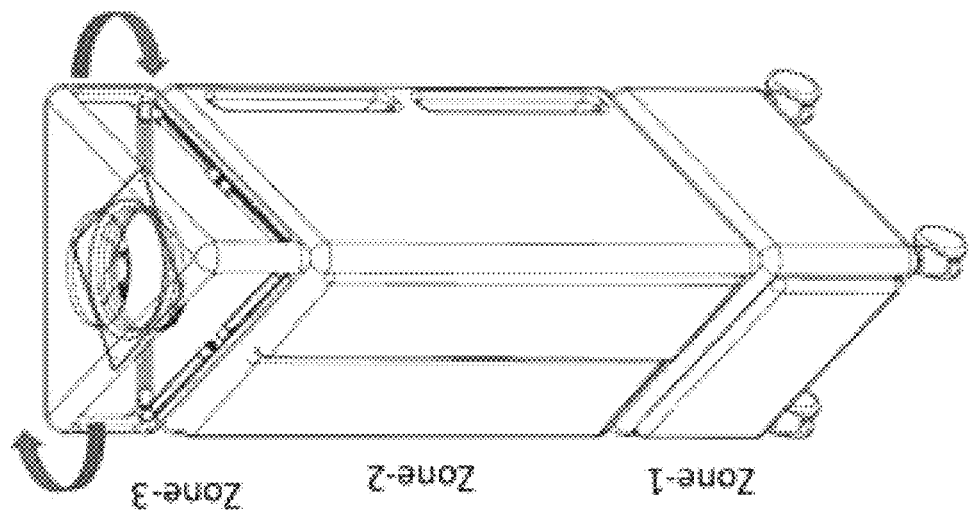
Figure 6:
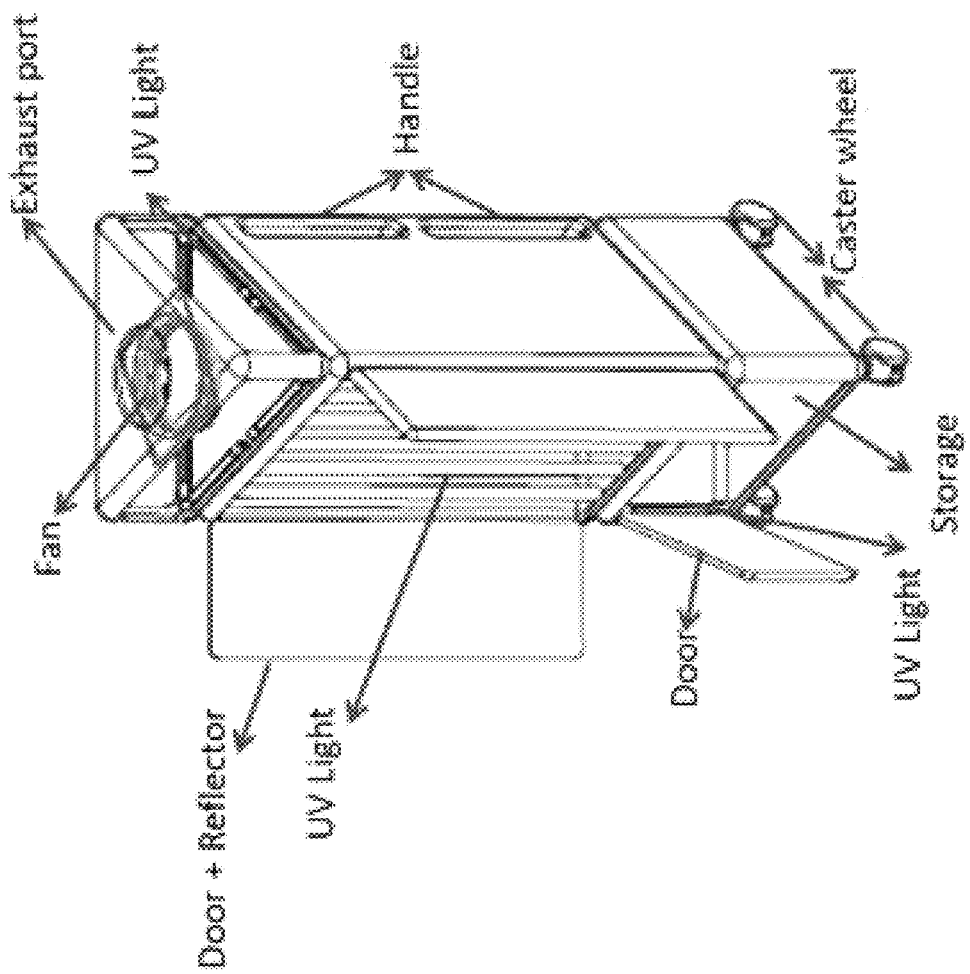
FIG. 6 shows the system in a closed condition.

The unit 300 has various handles 318 and doors/reflectors 320 that open up access for a chamber that has a plurality of UCV lamps 322 to expose the environment to UV light (FIG. 5). In one embodiment, a mirror is positioned on the inside of the door 320 so that the mirror can reflect UV light when the door is opened, as shown in FIG. 5. FIG. 6 shows the unit 300 in a closed condition, where all doors are sealed and no UV radiation is emitted from the bottom two zones. However, the top zone is still operational even in the closed condition. The door material can use mirror or glass to passthrough the UVC. Plain glass will absorb some percentage. Mirrors will also absorb, but again depends on the mirror backing material. Preferably, the mirrors on the back of the doors are metallic reflectors with special coatings that offer very high transmittivity for UV light.

The unit 300 has a power button 324 that provides power from a battery 328 to the air pumps and UV lamps 332. A charging port 326 allows the battery 328 to be recharged.

To provide mobility, a plurality of 360 deg wheels are provided on the bottom of the unit 300. Above the wheels is the third chamber with UV lamps 332. When the door of the third chamber is opened, a mirror on the back of the door reflects the UV light throughout the facility to kill molds.

Figure 4:
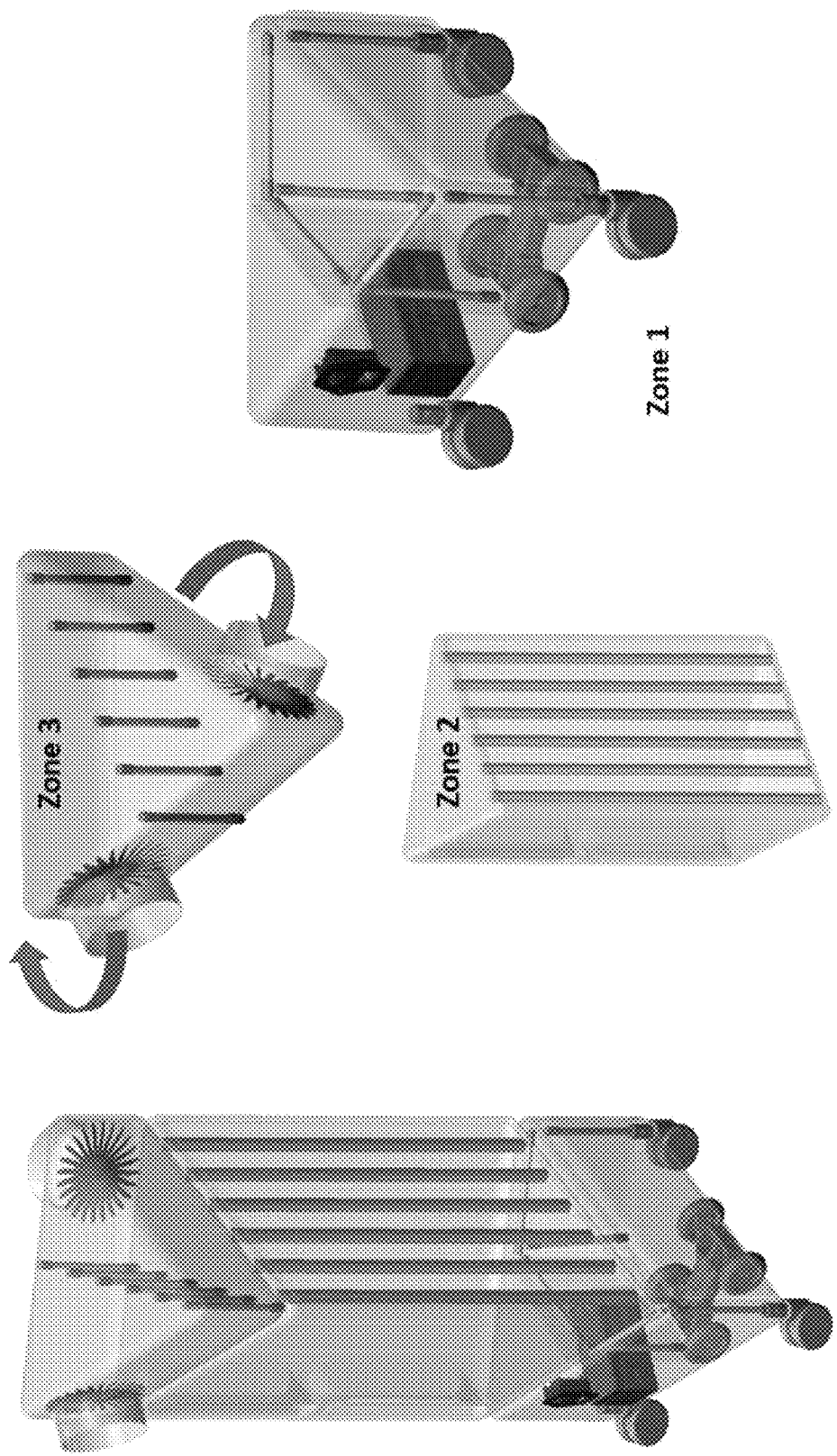
FIG. 4 shows the individual system components including the first, second and third components and the UV lamps that kill molds.

FIG. 4 shows the individual system components including the first, second and third components and the UV lamps that kill molds. In one embodiment the present invention provides a method for controlling, especially for significantly reducing, pathogen growth on one or more living plants, especially on a plurality of plants (or on one or more parts thereof, such as the lower half or lower ⅓rd or ¼th of the plant), by contacting at least one or more aerial parts of said plants periodically with UV-C light for a time and at a proximity and intensity sufficient to control one or more pathogens. The UV-C light has especially a negative effect on the pathogen(s), and preferably reduces the amount of pathogens in the area treated. For example, all or part of the fungal mycelium which comes into contact with the UV-C light may be killed, whereby the overall disease pressure on the plurality of plants is reduced. Thus, the pathogens' growth, viability and/or infectivity and/or reproduction may be reduced by the UV-C treatment. Thereby, the yield of the plurality of plants is increased compared to control plants which were not treated in the same way (provided that the initial disease pressure to which the plants were exposed was similar). In a preferred embodiment the growth and development of the plant or of the plurality of plants is not affected negatively by the UV-C treatment, and the yield is also not affected negatively, and is most preferably significantly increased compared to control plants.

In one embodiment of the invention the plant tissue exposed to the UV-C light is not damaged (see below), while in another embodiment some plant tissue parts may be damaged by the UV-C light (e.g. the lower leaves exposed to the UV-C may show UV-C induced symptoms or even die-off or "burn"; see further below), while the overall plant growth and yield are not affected negatively (i.e. the plants continue growing normally and the yield is at least identical to, but preferably at least 1%, 2%, 3%, 4%, 5%, 10%, 20%, 30%, 40%, 50%, 60%, or more, higher than for control plants).

In another embodiment the present invention provides a method for significantly reducing pathogen damage (i.e. protecting plants against pathogen damage) of one or more living plants (a plurality of plants), by exposing at least aerial parts of said plants which are sensitive to be infected by pathogens, one or more times (periodically) to UV-C light for a time and at a proximity and intensity sufficient to have an effect on (i.e., control, especially reduce) the pathogen growth (e.g. reducing the viability and/or infectivity and/or reproduction) without damaging the plant tissue.

Especially provided is a method for reducing plant tissue damage caused by one or more plant pathogens, whereby the method comprises exposing live plants (or parts thereof) one or more times with an amount of UV-C light which is high enough to reduce plant tissue damage caused by said pathogen(s) but which is low enough to not result in permanent damage of said plant tissue. Especially, growth and yield of the plants are not affected negatively.

The resulting system offers the following advantages. The modular nature of the system can be built into various sizes to cater to small and large grow spaces. The system offers fast cycles that allow for quick turnover time with respect to the installation and operations. The system minimizes customer concerns about poor staff compliance with cleaning protocols.

The three chambers handle problem points when seeds are carriers for mold spores and pose risk for further mold propagation. Disinfection is done through ultraviolet light exposure to achieve kill on potential spores without causing death to the seed. Further, some form of mold spores can be airborne and present in the air. To destroy this risk, ultraviolet light air circulation can eliminate spores. In the growing phase, a UV Room Disinfection unit or overhead/wall lighting system to be used to kill surface mold within the room or on plants. In the drying phase, the ultraviolet light chamber can be utilized for buds to be placed in and kill and spores still present or that may be newly formed. The system can destroy the following main categories of Mold that affect *Cannabis:*

*ASPERGILLUS*: The fungus' spores are present in the air and can cause damage in the range of a slight odor, spoilage, or to significant illness.

*PENICILLIUM*: *Penicillium* is found world-wide and can ruin fruit crops or infect and harm animals and humans.

*RHIZOPUS*: This genus has about 10 species of fungi, the majority of which are decomposers that feed on a variety of dead organic matter. However, some species are parasitic or pathogenic.

*MUCOR*: Often found in soil and known to thrive in cooler environments, there are over 50 species.

*BOTRYTIS*: Since often afflicting plants, this mold coined the term bud rot. "Noble Rot" or dry rot is sometimes beneficial and is often used to enhance the flavor of some wines. Wet rot is a devastating killer for entire crops of strawberries, tomatoes, rhubarb, and *cannabis.*

The embodiments described above for plants thus equally apply for the treatment of cuttings. Suitably, cuttings are contacted with a suitable dosage of UV-C light at one or more timepoints after they are removed from the stock (parent) *cannabis* plant and before they are planted into soil or a suitable growth or rooting medium. The treatment may also be applied at one or more timepoints after the cutting is placed into soil or a suitable growth or rooting medium. The rooting time varies depending on the species. Especially, contact before and/or during rooting and/or optionally even thereafter, during further growth, is suitable for controlling pathogen damage and/or for reducing loss of viability of the cutting. Also the rooting success (% of cuttings which successfully form roots and can develop into mature plants) can be increased significantly using UV-C light, preferably by at least 5%, 10%, 20%, or more, compared to non-treated cuttings.

Thus, in one embodiment the whole cutting, and/or the aerial part of the cutting (after placement into a suitable medium or after transplantation to other medium or into the field) is contacted one or more times with UV-C light of the dosages described above.

The foregoing detailed description of the invention has been presented for purposes of illustration and description. It is not intended to be exhaustive or to limit the invention to the precise form disclosed, and obviously many modifications and variations are possible in light of the above teaching. For example, for treating little trees planted in rows in open field, the system could span more than one row. In that case the light sources are positioned such that in each row between two rows of trees a light source will be present, so as to enable to treat more than one row simultaneously. The described embodiments were chosen in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:
1. A mold disinfection system, comprising:
a first compartment with an air inlet, an air pump to circulate air, a UVC lamp to disinfect mold in the circulated air, and an air outlet;
a second compartment with one or more doors and a mirror on each door to reflect UVC radiation;

a third compartment with a door and a mirror on the back of the door to reflect UVC radiation;

a series of high powered UVC lamps that are positioned towards an outer wall of the system, wherein the UVC lamps are covered by another layer of plastic or sheet metal enclosure to prevent accidental damage and unwanted UVC exposure to humans;

wheels extending from one of the compartments to move the system; and electronics controlling the UVC lamps and the air pump and communicating with a mobile device to receive operating instructions therefrom.

2. The system of claim 1, wherein the mobile device comprises an application to remotely control UVC radiation emitters.

3. The system of claim 2, wherein the application controls contact time or exposure of UVC light with the contaminant and UVC output and intensity.

4. The system of claim 2, wherein the application captures utilization data, including treatment time, location usage, and operator statistics.

5. The system of claim 2, wherein the application tracks delivered dose and utilization data in real time.

6. The system of claim 2, wherein the application calculates a dose to be delivered, where dose is determined based on UVC intensity and time of exposure to the UVC based on room dimensions.

7. The system of claim 6, wherein the application turns on the UVC lamps on a timed interval.

8. The system of claim 2, wherein the application receives data including UV Dosage, Operator Name, Room Number, and Time/Date.

9. The system of claim 2, wherein the application is synced with an existing schedule or to create a new schedule towards any Contamination Control Program as devised by a Grow Facility or defined by a State Regulator.

10. The system of claim 1, comprising sensors on an emitter that measures light reflected back to the device from surfaces within a room.

11. The system of claim 1, comprising remote wireless sensors placed in different targeted areas of a room to measure incident light (both reflective and direct) and therefore actual dose delivered.

12. The system of claim 11, wherein the measured light is reflective light or direct light.

13. The system of claim 1, wherein the third compartment is used for enclosed sanitization.

14. The system of claim 1, comprising seeds placed inside the third compartment and one or more UVC lamps that are placed radially, or other desired configuration, for enabling the seeds and buds during curing to experience 360 degrees of direct UVC coverage.

15. The system of claim 1, wherein the second compartment performs Open Space Sanitization.

16. The system of claim 1, wherein the first compartment is used for Enclosed Sanitization.

17. The system of claim 1, wherein seeds are placed inside the first compartment, which consists of a series of UVC lamps that are placed radially, or other desired configuration, thereby enabling the seeds and buds (during curing) to experience 360 degrees of direct UVC coverage.

18. The system of claim 1, comprising a rapid room turnover.

19. The system of claim 1, wherein faster use times lead to more rapid room turnover.

* * * * *